United States Patent
Seo et al.

(10) Patent No.: US 9,127,104 B2
(45) Date of Patent: Sep. 8, 2015

(54) POLYMERIZABLE LIQUID CRYSTAL COMPOUND, A LIQUID CRYSTAL COMPOSITION COMPRISING THE COMPOUND, AND AN OPTICALLY ANISOTROPIC BODY

(71) Applicant: LG Chem, Ltd., Seoul (KR)

(72) Inventors: Kyung Chang Seo, Daejeon (KR); Sung-Ho Chun, Daejeon (KR); Dai Seung Choi, Daejeon (KR); Mi-Ra Hong, Gangwon-do (KR); Hyeong Bin Jang, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

(21) Appl. No.: 14/355,898

(22) PCT Filed: Jun. 25, 2013

(86) PCT No.: PCT/KR2013/005608
§ 371 (c)(1),
(2) Date: May 2, 2014

(87) PCT Pub. No.: WO2014/003416
PCT Pub. Date: Jan. 3, 2014

(65) Prior Publication Data
US 2015/0099820 A1    Apr. 9, 2015

(30) Foreign Application Priority Data
Jun. 28, 2012 (KR) .................. 10-2012-0070200

(51) Int. Cl.
C08F 22/20 (2006.01)
C09K 19/22 (2006.01)
C09K 19/32 (2006.01)
C07C 251/24 (2006.01)
C09K 19/04 (2006.01)

(52) U.S. Cl.
CPC .............. *C08F 22/20* (2013.01); *C07C 251/24* (2013.01); *C09K 19/22* (2013.01); *C09K 19/322* (2013.01); *C09K 2019/0448* (2013.01)

(58) Field of Classification Search
CPC .... C07C 251/18; C07C 251/24; C09K 19/22; C09K 19/322; C09K 2019/0448; C09K 2019/2078; G02B 5/30; C08F 22/20
See application file for complete search history.

(56) References Cited

U.S. PATENT DOCUMENTS

| | | | |
|---|---|---|---|
| 6,136,225 A | 10/2000 | Meyer et al. | |
| 8,262,932 B2* | 9/2012 | Katoh et al. | ............. 252/299.01 |
| 2009/0306196 A1* | 12/2009 | Lehn et al. | ................... 514/449 |
| 2010/0297367 A1 | 11/2010 | Hirai et al. | |
| 2011/0051050 A1 | 3/2011 | Shin et al. | |

FOREIGN PATENT DOCUMENTS

| | | |
|---|---|---|
| CN | 100572502 C | 12/2009 |
| JP | 2009-029929 A | 2/2009 |
| JP | 2011-195795 A | 10/2011 |
| KR | 10-2009-0041385 A | 4/2009 |
| KR | 10-2010-0014882 A | 2/2010 |
| KR | 10-2010-0126182 A | 12/2010 |
| KR | 10-2011-0040789 A | 4/2011 |
| KR | 10-1136495 B1 | 4/2012 |

OTHER PUBLICATIONS

CAPLUS 2006: 594467.*

* cited by examiner

*Primary Examiner* — Shean C Wu
(74) *Attorney, Agent, or Firm* — Dentons US LLP

(57) ABSTRACT

The present invention relates to a polymerizable liquid crystal compound, a liquid crystal composition including the same, and an optically anisotropic body. The polymerizable liquid crystal compound according to the present invention has not only high birefringence but also excellent coating orientation, and thus it is possible to prepare a optically anisotropic body which is thin but superior in optical properties.

10 Claims, 2 Drawing Sheets

| Compound | Degree of Light Leakage | Compound | Degree of Light Leakage |
|---|---|---|---|
| RM-01 |  | RM-02 |  |
| RM-03 |  | RM-04 |  |
| RM-05 |  | RM-06 |  |
| RM-07 |  | RM-08 |  |

| Compound | Degree of Light Leakage | Compound | Degree of Light Leakage |
|---|---|---|---|
| RM-09 |  | RM-10 |  |
| RM-11 |  | RM-12 |  |
| RM257 |  | - | - |

POLYMERIZABLE LIQUID CRYSTAL COMPOUND, A LIQUID CRYSTAL COMPOSITION COMPRISING THE COMPOUND, AND AN OPTICALLY ANISOTROPIC BODY

This application is a National Stage of International Patent Application No. PCT/KR2013/005608, filed on Jun. 25, 2013, and claims the benefit of Korean Patent Application Nos. 10-2012-0070200, filed on Jun. 28, 2012 and 10-2013-0072986, filed on Jun. 25, 2013, in the Korean Intellectual Property Office, all of which are incorporated herein by reference in their entirety.

BACKGROUND OF THE INVENTION (a) Field of the Invention

The present invention relates to a polymerizable liquid crystal compound, a liquid crystal composition including the same, and an optically anisotropic body.

(b) Description of the Related Art

A phase retarder is a type of optical element changing the polarization state of light passing through the same, and equally said a wave plate. When a light passes through an electromagnetic phase retarder, the polarization direction (direction of electric field vector) becomes a sum of two elements (an ordinary ray and an extraordinary ray) parallel or perpendicular to the optic axis, and changes after passing the phase retarder because the vector sum of two elements varies according to the birefringence and the thickness of the phase retarder.

Recently, one of big issues of preparing optical film which can be used to the phase retarder is to prepare a high performance film at a small charge. Because, when liquid crystal compounds having high birefringence are used for preparing an optical film, it is possible to realize the necessary retardation value with small quantity of liquid crystal compounds. And, when such liquid crystal compounds are used, it is possible to prepare a thinner folial film.

Therefore, many studies for obtaining the liquid crystal compounds having high birefringence have been carried out actively, but there was a limitation on applying them to the industry in practice because of the orientation problem of the membrane when prior liquid crystal compounds were coated on a film.

SUMMARY OF THE INVENTION

Therefore, it is an aspect of the present invention to provide a polymerizable liquid crystal compound having high birefringence and showing excellent orientation when it is coated.

It is another aspect of the present invention to provide a polymerizable liquid crystal composition including the compound.

It is still another aspect of the present invention to provide an optically anisotropic body including the polymer prepared from the polymerizable liquid crystal composition.

According to the present invention, a polymerizable liquid crystal compound represented by Chemical Formula 1 is provided:

[Chemical Formula 1]

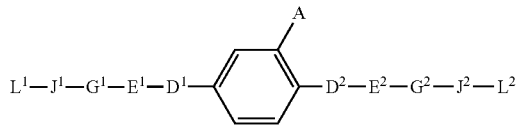

in Chemical Formula 1,

A is a $C_1$-$C_{10}$ alkyl group;

$D^1$, $D^2$, $G^1$, and $G^2$ are independently a single bond or a divalent connecting group, and at least one of $D^1$, $D^2$, $G^1$, and $G^2$ is an imine group;

$E^1$ and $E^2$ are independently benzene ring or naphthalene ring, and at least one of $E^1$ and $E^2$ is naphthalene ring;

$J^1$ and $J^2$ are independently a $C_1$-$C_{10}$ alkylene group; and $L^1$ and $L^2$ are independently hydrogen or a polymerizable group.

Furthermore, according to another embodiment of the present invention, a polymerizable liquid crystal composition including the compound represented by Chemical Formula 1 is provided.

And, according to still another embodiment of the present invention, an optically anisotropic body including a hardened material or polymer of the polymerizable liquid crystal compound is provided.

EFFECTS OF THE INVENTION

The polymerizable liquid crystal compound according to the present invention has not only high birefringence but also excellent coating orientation, and thus it can provide an optically anisotropic body which is thin but superior in optical properties.

DETAILED DESCRIPTION OF THE EMBODIMENTS

Figure 1:
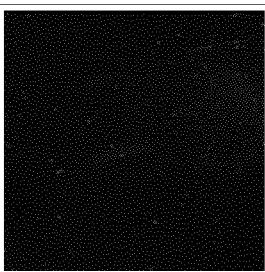
FIGS. 1 and 2 are photos of the retardation films including the compounds of Examples and Comparative Examples taken by the method of Experimental Example 2 in order to check the light leakage.
Figure 1:
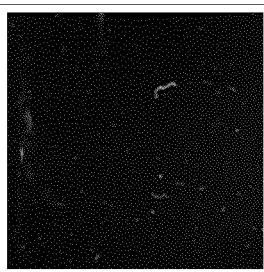
Figure 1:
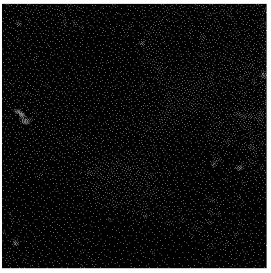
Figure 1:
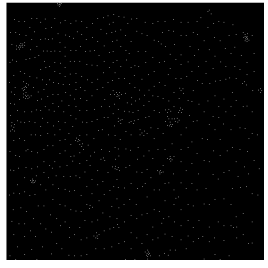
Figure 1:
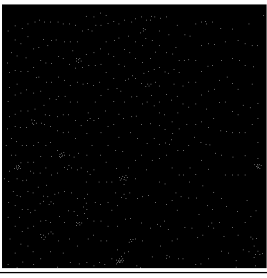
Figure 1:
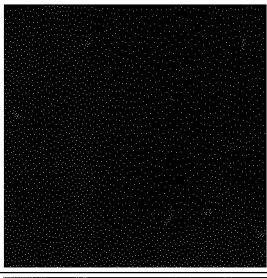
Figure 1:
Figure 1:

Hereinafter, the polymerizable liquid crystal compound, the polymerizable liquid crystal composition including the same, and the optically anisotropic body according to the embodiments of the present invention are explained in more detail.

Before that, unless there is overt mention about them in the present specification, technical terms used in the specification are just for representing a specific embodiment and they are not intended to limit the present invention.

And, the singular words used here include plural meaning unless the words represent apparent opposite meaning.

And, the meaning of 'include' used in the present specification specifies specific characteristics, territories, essences, steps, motions, elements, or components, and it does not exclude the addition of other specific characteristics, territories, essences, steps, motions, elements, or components.

Meanwhile, the 'polymerizable liquid crystal compound' is a liquid crystal compound having a polymerizable group, and it is possible to prepare a polymer having a fixed orientation structure of liquid crystal molecules by exposing the compound to an active energy ray after aligning a liquid crystal composition including at least one of the polymerizable liquid crystal compound in a liquid crystal state. The polymer obtained like this shows anisotropy in physical properties such as refractive index, dielectric constant, magnetic susceptibility, modulus, thermal expansion rate, and so on. And, for example, it may be applied to an optically anisotropic body such as a retardation plate, a polarizing plate, a polarizing prism, a brightness enhancing film, a covering material of optical fiber, and so on. And, for example, the properties such as transparency, strength, coatability, solubility, crystallinity, heat resistance, and so on are important besides the anisotropy of the polymer.

As the result of repeating studies for the liquid crystal compound, the present inventors found that the polymerizable liquid crystal compound having the chemical structure like the following Chemical Formula 1, specifically the polymerizable liquid crystal compound having a center benzene ring substituted by an alkyl, and at least one imine group and at least one naphthalene group at the same time in the main chain, has not only high birefringence but also excellent orientation in coating process, and makes it possible to prepare an optically anisotropic body having excellent optical properties with thin thickness, and accomplished the present invention.

According to one embodiment of the present invention, the polymerizable liquid crystal compound represented by the following Chemical Formula 1 is provided:

[Chemical Formula 1]

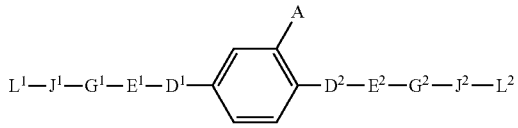

in Chemical Formula 1,

A is a $C_1$-$C_{10}$ alkyl group;

$D^1$, $D^2$, $G^1$, and $G^2$ are independently a single bond or a divalent connecting group, and at least one of $D^1$, $D^2$, $G^1$, and $G^2$ is an imine group;

$E^1$ and $E^2$ are independently benzene ring or naphthalene ring, and at least one of $E^1$ and $E^2$ is naphthalene ring;

$J^1$ and $J^2$ are independently a $C_1$-$C_{10}$ alkylene group; and $L^1$ and $L^2$ are independently hydrogen or a polymerizable group.

The polymerizable liquid crystal compound represented by Chemical Formula 1 may have a structure that at least one imine connecting group is introduced to a mesogen compound to which a condensed ring is introduced, and thus it can exhibit high birefringence and show excellent orientation when it is coated.

According to the present invention, A in Chemical Formula 1 is a substituent connected to the center benzene ring of the compound, and can make the polymerizable liquid crystal compound have more excellent orientation and reduce the light leakage of the retardation film prepared by using the same. According to one embodiment, said A may be a $C_1$-$C_{10}$ alkyl group, preferably a $C_1$-$C_6$ alkyl group, and more preferably a $C_1$-$C_3$ alkyl group.

And, in Chemical Formula 1, $D^1$, $D^2$, $G^1$, and $G^2$ may be independently a single bond or a divalent connecting group. Here, the 'divalent connecting group' may be —CH=N—, —O—, —S—, —CO—, —COO—, —OCO—, —O—COO—, —CO—NR—, —NR—CO—, —NR—CO—NR—, —OCH$_2$—, —CH$_2$O—, —SCH—, —CH$_2$S—, —CF$_2$O—, —OCF$_2$—, —CF$_2$S—, —SCF$_2$—, —CH$_2$CH$_2$—, —(CH$_2$)$_3$—, —(CH$_2$)$_4$—, —CF$_2$CH$_2$—, —CH$_2$CF$_2$—, —CF$_2$CF$_2$—, —C=C—, or —C≡C—, and said R may be independently hydrogen or a $C_1$-$C_{10}$ alkyl group.

Specifically, according to the present invention, at least one of $D^1$, $D^2$, $G^1$, and $G^2$ may be imine group (—CH=N—), and preferably each of $D^1$ and $D^2$, or $G^1$ and $G^2$ may be imine group respectively. Since the polymerizable liquid crystal compound of said embodiment includes at least one imine group, it may show at least one peak at the chemical shift (δ) of 8.0 ppm to 8.5 ppm in $^1$H NMR spectrum.

Furthermore, each of $E^1$ and $E^2$ in Chemical Formula 1 is independently benzene ring or naphthalene ring, and at least one of $E^1$ and $E^2$ may be naphthalene ring, and preferably, each of $E^1$ and $E^2$ may be naphthalene ring.

Namely, the polymerizable liquid crystal compound of one embodiment has a center benzene ring to which an alkyl substituent is introduced, and specifically, has a structure that at least one imine connecting group and at least one naphthalene ring connecting group are introduced to the main chain at the same time. According to this, the polymerizable liquid crystal compound of one embodiment can show not only higher birefringence due to the synergy of the substituent and the connecting groups but also superior orientation of the composition including the same when it is coated. Therefore, the compound makes it possible to prepare an optically anisotropic body which is thin but superior in optical properties.

Meanwhile, in Chemical Formula 1, said $J^1$ and $J^2$ may be independently a $C_1$-$C_{10}$ alkylene group, preferably a $C_2$-$C_9$ alkylene group, and more preferably a $C_3$-$C_6$ alkylene group.

And, in Chemical Formula 1, said $L^1$ and $L^2$ may be independently hydrogen or a polymerizable group. Here, the 'polymerizable group' can be defined as any cross-linkable or polymerizable functional group such as a unsaturated bond and (meth)acrylate group. According to the present invention, said $L^1$ and $L^2$ may be independently hydrogen, an acrylate, a methacrylate, an epoxy, and so on.

Specific examples of the polymerizable liquid crystal compound of Chemical Formula 1 may be represented by the following Chemical Formulae 2a and 2b. In Chemical Formulae 2a and 2b, $R^1$ and $R^2$ may be independently a $C_1$-$C_{10}$ alkyl group and n may be an integer of 1 to 10. However, the polymerizable liquid crystal compound of the present invention is not limited by or to the following exemplified compounds.

[Chemical Formula 2a]

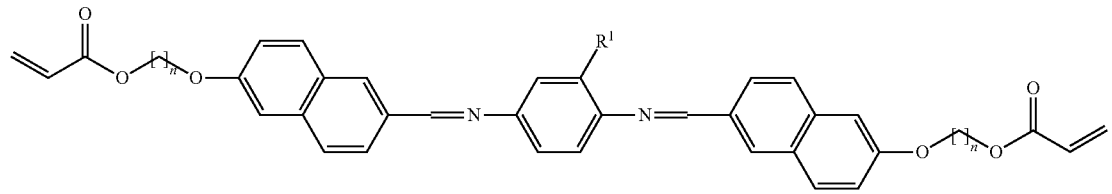

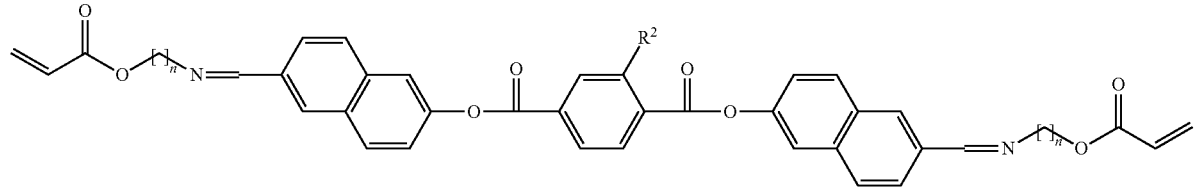

[Chemical Formula 2b]

Meanwhile, the polymerizable liquid crystal compound represented by Chemical Formula 1 may be prepared by applying a known reaction, and more detailed preparation method will be disclosed in Examples of the present specification.

According to another embodiment of the present invention, the polymerizable liquid crystal composition including the compound represented by Chemical Formula 1 is provided.

The composition according to the present invention includes the compound represented by Chemical Formula 1 which is a polymerizable liquid crystal monomer, and can be homopolymerized or copolymerized by using the compound of Chemical Formula 1 alone or in combination.

The composition may further include an arbitrary liquid crystal compound in addition to the compound of Chemical Formula 1, and the arbitrary liquid crystal compound may have a polymerizable property or not. Here, for example, the arbitrary liquid crystal compound may be a liquid crystal compound having an ethylenically unsaturated bond, a compound having an optical active group, a rod-like liquid crystal compound, and the like.

At this time, the arbitrary liquid crystal compounds may be mixed with a proper amount according to their structure. Preferably, it is advantageous in the aspect of achieving the object of the present invention that the content of the compound of Chemical Formula 1 is 60 wt % or more per the total monomer weight.

The polymerizable liquid crystal composition may further include an additive such as a solvent, a polymerization initiator, a stabilizer, a liquid crystal orientation agent, a dye, a pigment, and so on. The additive may be a common component in the technical field to which the present invention pertains, and the details are not limited.

On the other hand, according to still another embodiment of the present invention, an optically anisotropic body including a hardened material or polymer of the polymerizable liquid crystal compound of Chemical Formula 1 is provided.

The optically anisotropic body may include a hardened material or polymer in which at least part of the end polymerizable groups of the polymerizable liquid crystal compound of Chemical Formula 1 is addition-polymerized or cross-linked.

Specifically, as the optically anisotropic body according to the present invention includes the hardened material or polymer of the polymerizable liquid crystal compound, the light leakage phenomenon can be disappeared or minimized with high retardation value. Furthermore, the optically anisotropic body according to the present invention is thinner than prior laminate type optically anisotropic body and can be prepared by more simplified process.

Meanwhile, the optically anisotropic body may be prepared by coating and drying the polymerizable liquid crystal composition on a substrate, aligning the liquid crystal compound, and polymerizing the same by UV irradiation.

Here, the substrate is not limited particularly but a glass plate, a poly(ethyleneterephthalate) film, a cellulose-based film, and so on may be used. In the process of coating the polymerizable liquid crystal composition on the substrate, any known methods can be used without particular limitation, and for example, a roll coating method, a spin coating method, a bar coating method, a spray coating method, and so on can be used.

And, in the process of aligning the polymerizable liquid crystal composition, any known methods can be used, for example, a method of rubbing the composition layer formed or a method of applying a magnetic field or an electric field to the composition layer formed may be used.

The thickness of the optically anisotropic body may be adjusted according to its use, and preferably it may be in the range of 0.01 to 100, In Such optically anisotropic body of the present invention may be used as an optical element such as a retardation film of liquid crystal display device, an optical compensation plate, an alignment layer, a polarizing plate, a viewing angle magnification plate, a reflective film, a color filter, a holographic element, a light polarizing prism, an optical head, and the like.

Hereinafter, the function and effects of the present invention is explained in more detail by referring to specific examples of the present invention. However, the following examples are only for the understanding of the present invention and the scope of the present invention is not limited to or by them.

[Scheme 1: Examples 1 ~ 10]

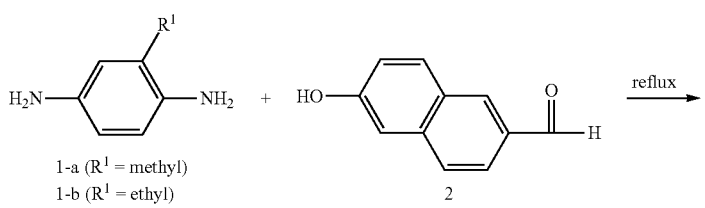

1-a ($R^1$ = methyl)
1-b ($R^1$ = ethyl)

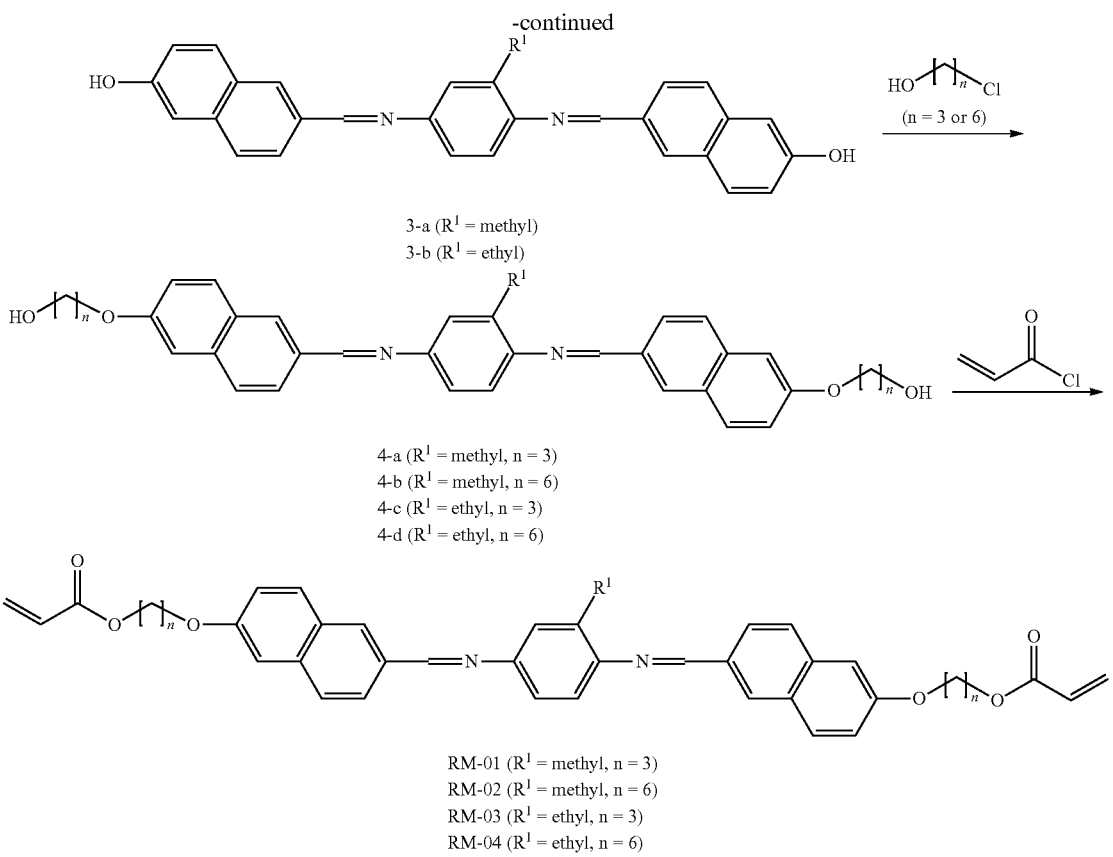

3-a ($R^1$ = methyl)
3-b ($R^1$ = ethyl)

4-a ($R^1$ = methyl, n = 3)
4-b ($R^1$ = methyl, n = 6)
4-c ($R^1$ = ethyl, n = 3)
4-d ($R^1$ = ethyl, n = 6)

RM-01 ($R^1$ = methyl, n = 3)
RM-02 ($R^1$ = methyl, n = 6)
RM-03 ($R^1$ = ethyl, n = 3)
RM-04 ($R^1$ = ethyl, n = 6)

Example 1

Synthesis of Compound 3-a

In Scheme 1, about 8 g of 2-methylbenzene-1,4-diamine (compound 1-a) [Journal of Chemical Research, 2005, 2, 123] was dissolved in about 80 ml of ethanol and the solution was heated to about 90° C. A solution that about 40 g of 6-hydroxy-2-naphthaldehyde (compound 2) was dissolved in about 150 ml of ethanol was added thereto in drops, and the mixture was stirred and refluxed for about 8 hrs. The reacted mixture was cooled to room temperature and a solid product was obtained. About 24 g of compound 3-a ($R^1$=methyl) was obtained by filtering the product with ethanol and vacuum drying the same.

Example 2

Synthesis of Compound 3-b

About 31 g of compound 3-b ($R^1$=ethyl) was obtained substantially according to the same method and condition as in Example 1, except that 2-ethylbenzene-1,4-diamine (compound 1-b) was used instead of compound 1-a.

Example 3

Synthesis of Compound 4-a

After dissolving about 10 g of compound 3-a according to Example 1, about 6.6 g of 3-chloropropanol, and about 13 g of potassium carbonate in acetone, the solution was stirred and refluxed for about 24 hrs. After cooling the reacted mixture to room temperature, the product was filtered so as to eliminate the solid, and distilled under reduced pressure. And then, about 11.5 g of compound 4-a ($R^1$=methyl, n=3) was obtained by column chromatography purification.

Example 4

Synthesis of Compound 4-b

About 10.4 g of compound 4-b ($R^1$=methyl, n=6) was obtained substantially according to the same method and condition as in Example 3, except that 6-chlorohexanol was used instead of 3-chloropropanol.

Example 5

Synthesis of Compound 4-c

About 12 g of compound 4-c ($R^1$=ethyl, n=3) was obtained substantially according to the same method and condition as in Example 3, except that compound 3-b according to Example 2 was used instead of compound 3-a.

Example 6

Synthesis of Compound 4-d

About 12.5 g of compound 4-d ($R^1$=ethyl, n=6) was obtained substantially according to the same method and condition as in Example 3, except that compound 3-b according to Example 2 was used instead of compound 3-a and 6-chlorohexanol was used instead of 3-chloropropanol.

Example 7

Synthesis of Compound RM-01

After dissolving about 10 g of compound 4-a according to Example 3 in about 100 ml of dimethyl acetamide, the solution was cooled to about 0° C. After adding about 3.3 g of acryloyl chloride thereto in drops for 30 mins, the mixture was stirred at room temperature for about 2 hrs. The reacted solution was diluted with diethyl ether and washed with a sodium chloride aqueous solution. After collecting the organic part from the product and chemically drying the same, the solvent was eliminated by distillation under reduced pressure. The collected product was purified by column chromatography and about 11 g of compound RM-01 ($R^1$=methyl, n=3) was obtained.

NMR spectrum of compound RM-01 is as follows.

$^1$H NMR (CDCl$_3$, standard material TMS) δ(ppm): 8.39 (2H, s), 8.28 (2H, s), 7.96 (2H, d), 7.84 (2H, m), 7.60 (2H, m), 7.10 (7H, m), 6.41 (2H, dd), 6.03 (2H, dd), 5.82 (2H, dd), 4.12 (4H, m), 4.03 (4H, m), 2.36 (3H, s), 1.98 (2H, m).

And, the organization of compound RM-01 was observed with a polarizing microscope and the phase transition temperature was measured. As a result, when the temperature increased, the crystalline phase was changed into nematic phase at about 167° C. and isotropic liquid crystal phase appeared when the temperature exceeded about 181° C. In this way, it was recognized that compound RM-01 forms nematic phase in the temperature range of about 167° C. to 181° C.

Example 8

Synthesis of Compound RM-02

About 10.2 g of compound RM-02 ($R^1$=methyl, n=6) was obtained substantially according to the same method and condition as in Example 7, except that compound 4-b according to Example 4 was used instead of compound 4-a.

NMR spectrum of compound RM-02 is as follows.

$^1$H NMR (CDCl$_3$, standard material TMS) δ(ppm): 8.38 (2H, s), 8.26 (2H, s), 7.91 (2H, d), 7.81 (2H, m), 7.62 (2H, m), 7.16 (7H, m), 6.44 (2H, dd), 6.05 (2H, dd), 5.81 (2H, dd), 4.14 (4H, m), 4.06 (4H, m), 2.34 (3H, s), 1.71 (4H, m), 1.57 (4H, m), 1.29 (8H, m)

And, the organization of compound RM-02 was observed with a polarizing microscope and the phase transition temperature was measured. As a result, it was recognized that compound RM-02 forms nematic phase in the temperature range of about 170° C. to 185° C.

Example 9

Synthesis of Compound RM-03

About 11.9 g of compound RM-03 ($R^1$=ethyl, n=3) was obtained substantially according to the same method and condition as in Example 7, except that compound 4-c according to Example 5 was used instead of compound 4-a.

NMR spectrum of compound RM-03 is as follows.

$^1$H NMR (CDCl$_3$, standard material TMS) δ(ppm): 8.40 (2H, s), 8.27 (2H, s), 7.91 (2H, d), 7.82 (2H, m), 7.57 (2H, m), 7.11 (7H, m), 6.42 (2H, dd), 6.03 (2H, dd), 5.84 (2H, dd), 4.11 (4H, m), 4.00 (4H, m), 2.53 (2H, s), 1.94 (2H, m), 1.24 (3H, m)

And, the organization of compound RM-03 was observed with a polarizing microscope and the phase transition temperature was measured. As a result, it was recognized that compound RM-03 forms nematic phase in the temperature range of about 148° C. to 161° C.

Example 10

Synthesis of Compound RM-04

About 10.3 g of compound RM-04 ($R^1$=ethyl, n=6) was obtained substantially according to the same method and condition as in Example 7, except that compound 4-d according to Example 6 was used instead of compound 4-a.

NMR spectrum of compound RM-04 is as follows.

$^1$H NMR (CDCl$_3$, standard material TMS) δ(ppm): 8.41 (2H, s), 8.29 (2H, s), 7.95 (2H, d), 7.84 (2H, m), 7.62 (2H, m), 7.16 (7H, m), 6.43 (2H, dd), 6.01 (2H, dd), 5.81 (2H, dd), 4.14 (4H, m), 4.04 (4H, m), 2.58 (3H, s), 1.71 (4H, m), 1.54 (4H, m), 1.22 (8H, m)

And, the organization of compound RM-04 was observed with a polarizing microscope and the phase transition temperature was measured. As a result, it was recognized that compound RM-04 forms nematic phase in the temperature range of about 178° C. to 189° C.

[Scheme 2: Examples 11 ~ 20]

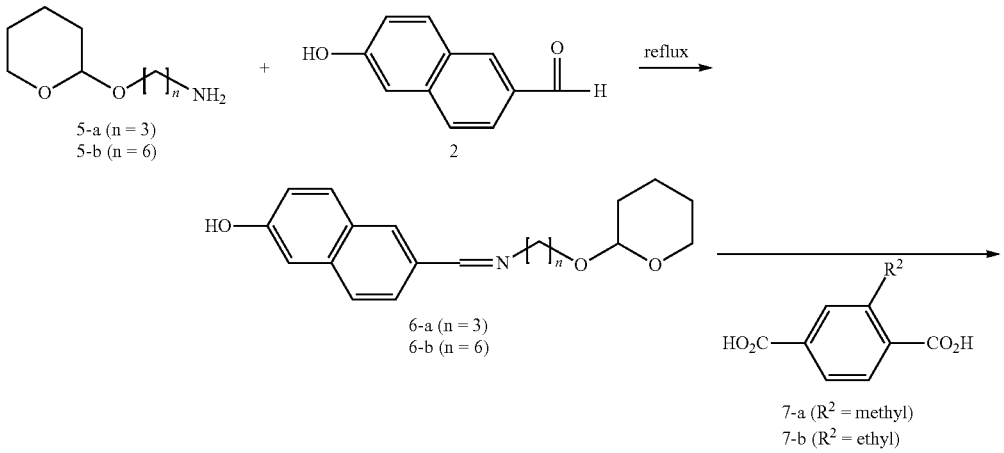

-continued

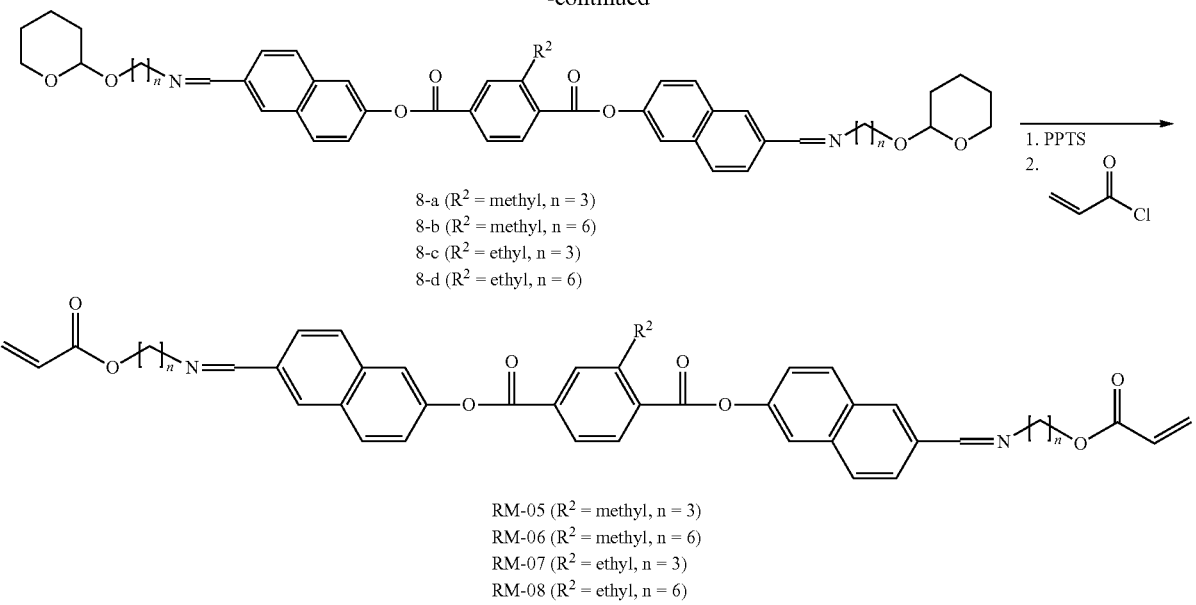

8-a (R² = methyl, n = 3)
8-b (R² = methyl, n = 6)
8-c (R² = ethyl, n = 3)
8-d (R² = ethyl, n = 6)

RM-05 (R² = methyl, n = 3)
RM-06 (R² = methyl, n = 6)
RM-07 (R² = ethyl, n = 3)
RM-08 (R² = ethyl, n = 6)

Example 11

Synthesis of Compound 6-a

In Scheme 2, about 8 g of compound 5-a [Journal of Medicinal Chemistry, 2008, 51, 17, 5176] was dissolved in about 80 ml of ethanol and the solution was heated to about 90° C. A solution that about 40 g of 6-hydroxy-2-naphthaldehyde (compound 2) was dissolved in about 150 ml of ethanol was added thereto in drops, and it was stirred and refluxed for about 8 hrs. The reacted mixture was cooled to room temperature and a solid product was obtained. About 22 g of compound 6-a (n=3) was obtained by filtering the product with ethanol and vacuum drying the same.

Example 12

Synthesis of Compound 6-b

About 27 g of compound 6-b (n=6) was obtained substantially according to the same method and condition as in Example 11, except that compound 5-b [Organic & Biomolecular Chemistry, 2008, 6, 7, 1176] was used instead of compound 5-a.

Example 13

Synthesis of Compound 8-a

After dissolving about 10 g of compound 6-a (n=3) according to Example 11, about 2.9 g of 2-methylterephthalic acid (compound 7-a (R²=methyl)) [Chem. Comm., 2011, 47, 18, 5244], and about 6.5 g of EDC (N-(3-dimethylaminopropyl)-N'-ethylcarbodiimide hydrochloride) in dichloromethane, the solution was cooled to about 0° C. After adding about 0.4 g of dimethyl aminopyridine and about 8 g of diisopropyl ethylamine thereto, the mixture was stirred for about 3 hrs. The reacted solution was diluted with dichloromethane, washed with 1N hydrochloric acid and brine, and chemically dried. The reacted product was obtained by filtration and distillation under reduced pressure. The collected product was purified by column chromatography and about 10.5 g of compound 8-a (R²=methyl, n=3) was obtained.

Example 14

Synthesis of Compound 8-b

About 12.4 g of compound 8-b (R²=methyl, n=6) was obtained substantially according to the same method and condition as in Example 13, except that compound 6-b (n=6) according to Example 12 was used instead of compound 6-a.

Example 15

Synthesis of Compound 8-c

About 11.5 g of compound 8-c (R²=ethyl, n=3) was obtained substantially according to the same method and condition as in Example 13, except that 2-ethylterephthalic acid (compound 7-b) was used instead of compound 7-a.

Example 16

Synthesis of Compound 8-d

About 10.4 g of compound 8-d (R²=ethyl, n=6) was obtained substantially according to the same method and condition as in Example 13, except that compound 6-b (n=6) according to Example 12 was used instead of compound 6-a and 2-ethylterephthalic acid (compound 7-b) was used instead of compound 7-a.

Example 17

Synthesis of Compound RM-05

After dissolving about 10 g of compound 8-a according to Example 13 and about 0.4 g of PPTS (pyridinium p-toluene sulfonate) in tetrahydrofuran, and the mixture was stirred and refluxed for about 2 hrs. And then, the reacted solution was distilled under reduced pressure so as to remove the solvent, and the remains were diluted with dichloromethane and washed with brine. The organic layer obtained like this was chemically dried and distilled under reduced pressure, and white solid compound was obtained.

After dissolving said white solid compound in about 100 ml of dimethyl acetamide, the solution was cooled to about 0° C. After adding about 3.3 g of acryloyl chloride thereto in drops for 30 mins, the mixture was stirred at room temperature for about 2 hrs. The reacted solution was diluted with diethyl ether and washed with a sodium chloride aqueous solution. After collecting the organic part from the product and chemically drying the same, the solvent was eliminated by distillation under reduced pressure. The collected product was purified by column chromatography and about 9.5 g of compound RM-05 ($R^2$=methyl, n=3) was obtained.

NMR spectrum of compound RM-05 is as follows.

$^1$H NMR (CDCl$_3$, standard material TMS) δ(ppm): 8.26 (2H, s), 8.12 (5H, m), 7.91 (2H, m), 7.77 (2H, m), 7.64 (2H, m), 6.99 (4H, m), 6.41 (2H, dd), 6.02 (2H, dd), 5.83 (2H, dd), 4.11 (4H, m), 3.53 (4H, m), 2.35 (3H, s), 1.91 (2H, m)

And, the organization of compound RM-05 was observed with a polarizing microscope and the phase transition temperature was measured. As a result, it was recognized that compound RM-05 forms nematic phase in the temperature range of about 153° C. to 177° C.

Example 18

Synthesis of Compound RM-06

About 10.1 g of compound RM-06 ($R^2$=methyl, n=6) was obtained substantially according to the same method and condition as in Example 17, except that compound 8-b according to Example 14 was used instead of compound 8-a.

NMR spectrum of compound RM-06 is as follows.

$^1$H NMR (CDCl$_3$, standard material TMS) δ(ppm): 8.23 (2H, s), 8.10 (5H, m), 7.89 (2H, m), 7.74 (2H, m), 7.61 (2H, m), 6.94 (4H, m), 6.38 (2H, dd), 6.00 (2H, dd), 5.80 (2H, dd), 4.12 (4H, m), 3.53 (4H, m), 2.34 (3H, s), 1.61 (8H, m), 1.29 (8H, m)

And, the organization of compound RM-06 was observed with a polarizing microscope and the phase transition temperature was measured. As a result, it was recognized that compound RM-06 forms nematic phase in the temperature range of about 150° C. to 184° C.

Example 19

Synthesis of Compound RM-07

About 9.8 g of compound RM-07 ($R^2$=ethyl, n=3) was obtained substantially according to the same method and condition as in Example 17, except that compound 8-c according to Example 15 was used instead of compound 8-a.

NMR spectrum of compound RM-07 is as follows.

$^1$H NMR (CDCl$_3$, standard material TMS) δ(ppm): 8.25 (2H, s), 8.10 (5H, m), 7.91 (2H, m), 7.74 (2H, m), 7.61 (2H, m), 7.01 (4H, m), 6.42 (2H, dd), 6.01 (2H, dd), 5.86 (2H, dd), 4.14 (4H, m), 3.51 (4H, m), 2.54 (5H, s), 1.94 (2H, m), 1.21 (3H, m)

And, the organization of compound RM-07 was observed with a polarizing microscope and the phase transition temperature was measured. As a result, it was recognized that compound RM-07 forms nematic phase in the temperature range of about 164° C. to 180° C.

Example 20

Synthesis of Compound RM-08

About 11.0 g of compound RM-08 ($R^2$=ethyl, n=6) was obtained substantially according to the same method and condition as in Example 17, except that compound 8-d according to Example 16 was used instead of compound 8-a.

NMR spectrum of compound RM-08 is as follows.

$^1$H NMR (CDCl$_3$, standard material TMS) δ(ppm): 8.26 (2H, s), 8.12 (5H, m), 7.89 (2H, m), 7.75 (2H, m), 7.64 (2H, m), 6.95 (4H, m), 6.38 (2H, dd), 6.01 (2H, dd), 5.81 (2H, dd), 4.15 (4H, m), 3.53 (4H, m), 2.53 (2H, s), 1.62 (8H, m), 1.28 (8H, m), 1.20 (3H, m)

And, the organization of compound RM-08 was observed with a polarizing microscope and the phase transition temperature was measured. As a result, it was recognized that compound RM-08 forms nematic phase in the temperature range of about 178° C. to 202° C.

[Scheme 3: Comparative Examples 1~6]

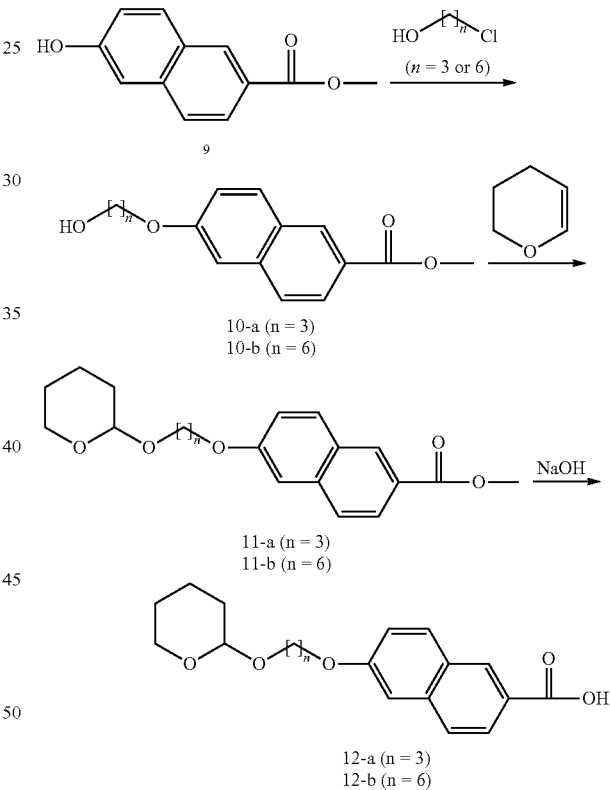

Comparative Example 1

Synthesis of Compound 10-a

In Scheme 3, after dissolving about 100 g of methyl 6-hydroxy-2-naphthoate (compound 9), about 94 g of 3-chloropropanol, and about 182 g of potassium carbonate in acetone, the mixture was stirred and refluxed for about 24 hrs. After cooling the reacted mixture to room temperature, the product was filtered so as to eliminate the solid, and distilled under reduced pressure. And then, about 132 g of compound 10-a (n=3) was obtained by column chromatography purification.

Comparative Example 2

Synthesis of Compound 10-b

About 110 g of compound 10-b (n=6) was obtained substantially according to the same method and condition as in Comparative Example 1, except that 6-chlorohexanol was used instead of 3-chloropropanol.

Comparative Example 3

Synthesis of Compound 11-a

After dissolving about 120 g of compound 10-a according to Comparative Example 1 and about 21 g of PPTS (pyridinium p-toluene sulfonate) in dichloromethane, the solution was cooled to about 0° C. After adding about 42 g of 3,4-dihydro-2H-pyran dissolved in dichloromethane thereto in drops, the mixture was stirred for about 12 hrs. After washing the reacted solution with brine and chemically drying the same, about 145 g of compound 11-a (n=3) was obtained by distilling the same under reduced pressure.

Comparative Example 4

Synthesis of Compound 11-b

About 110 g of compound 11-b (n=6) was obtained substantially according to the same method and condition as in Comparative Example 3, except that compound 10-b according to Comparative Example 2 was used instead of compound 10-a.

Comparative Example 5

Synthesis of Compound 12-a

After dissolving about 140 g of compound 11-a according to Comparative Example 3, sodium hydroxide (2M, 300 ml) was added thereto. The solution was stirred and refluxed for about 2 hrs, and distilled under reduced pressure. After dissolving the reaction product in water and dichloromethane, 3M hydrochloric acid was used so as to make the solution pH 5. The organic layer was separated from the solution, chemically dried, and distilled under reduced pressure, and about 107 g of white solid compound 12-a (n=3) was obtained by washing the same with hexane.

Comparative Example 6

Synthesis of Compound 12-b

About 89 g of compound 12-b (n=6) was obtained substantially according to the same method and condition as in Comparative Example 5, except that compound 11-b according to Comparative Example 4 was used instead of compound 11-a.

[Scheme 4: Comparative Example 7~10]

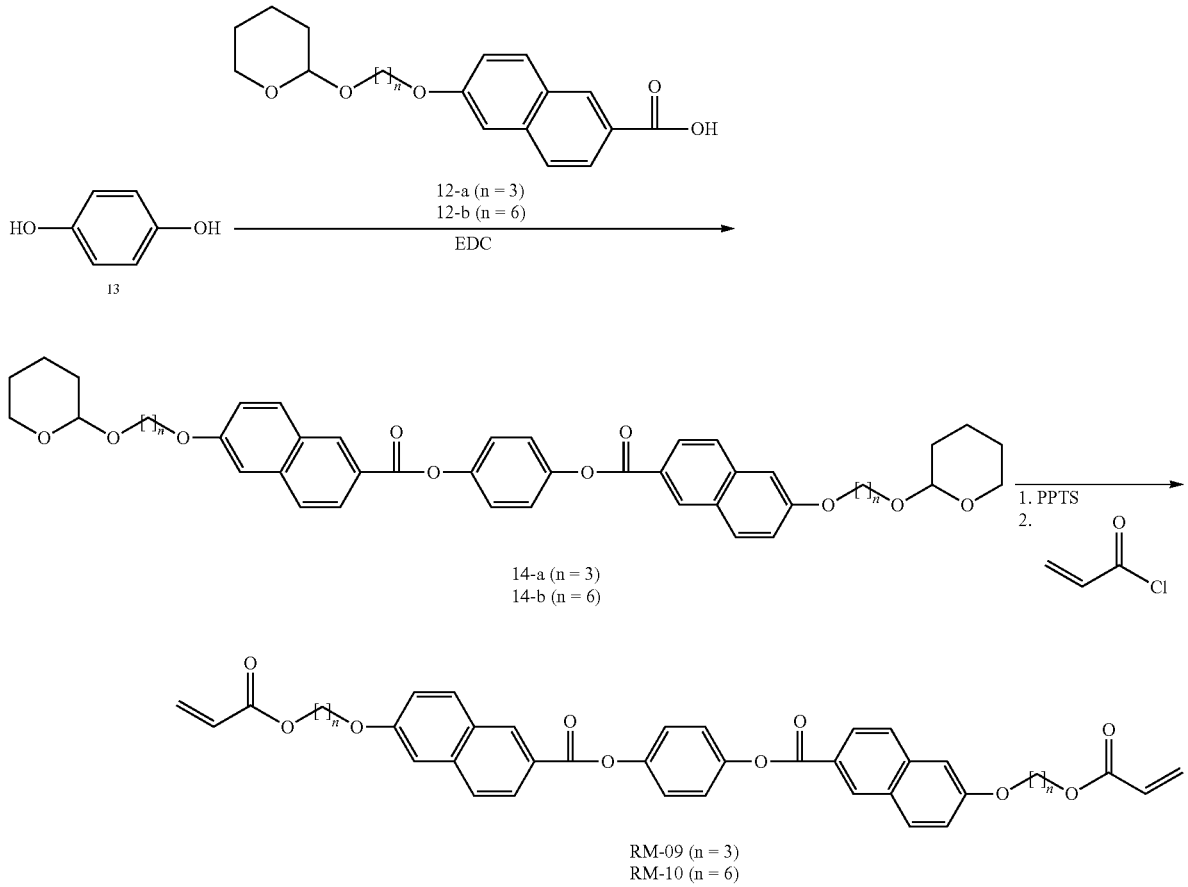

Comparative Example 7

Synthesis of Compound 14-a

After dissolving about 12.1 g of compound 12-a according to Comparative Example 5, about 3 g of hydroquinone, and about 7.2 g of EDC (N-(3-dimethylaminopropyl)-N'-ethyl-carbodiimide hydrochloride) in dichloromethane, the solution was cooled to about 0° C. After adding about 0.9 g of dimethyl aminopyridine and about 9 g of diisopropyl ethylamine thereto, the mixture was stirred for about 3 hrs. The reacted solution was diluted with dichloromethane, washed with 1N hydrochloric acid and brine, and chemically dried. The reacted product was obtained by filtration and distillation under reduced pressure. The collected product was purified by column chromatography and about 10.5 g of compound 14-a (n=3) was obtained.

Comparative Example 8

Synthesis of Compound 14-b

About 11.5 g of compound 14-b (n=6) was obtained substantially according to the same method and condition as in Comparative Example 7, except that compound 12-b according to Comparative Example 6 was used instead of compound 12-a.

Comparative Example 9

Synthesis of Compound RM-09

After dissolving about 10 g of compound 14-a according to Comparative Example 7 and about 0.4 g of PPTS (pyridinium p-toluene sulfonate) in tetrahydrofuran, and the mixture was stirred and refluxed for about 2 hrs. And then, the reacted solution was distilled under reduced pressure so as to remove the solvent, and the remains were diluted with dichloromethane and washed with brine. The organic layer obtained like this was chemically dried and distilled under reduced pressure, and white solid compound was obtained.

After dissolving said white solid compound in about 90 ml of dimethyl acetamide, the solution was cooled to about 0° C. After adding about 7 g of acryloyl chloride thereto in drops for 30 mins, the mixture was stirred at room temperature for about 2 hrs. The reacted solution was diluted with diethyl ether and washed with a sodium chloride aqueous solution. After collecting the organic part from the product and chemically drying the same, the solvent was eliminated by distillation under reduced pressure. The collected product was purified by column chromatography and about 12.0 g of compound RM-09 (n=3) was obtained.

NMR spectrum of compound RM-09 is as follows.

$^1$H NMR (CDCl$_3$, standard material TMS) δ(ppm): 8.52 (2H, s), 8.20 (2H, d), 7.75 (2H, d), 7.60 (2H, d), 7.22 (4H, s), 7.02 (4H, m), 6.44 (2H, dd), 6.09 (2H, dd), 5.90 (2H, dd), 4.04 (4H, m), 3.95 (4H, m), 1.99 (4H, m)

And, the organization of compound RM-09 was observed with a polarizing microscope and the phase transition temperature was measured. As a result, it was recognized that compound RM-09 forms nematic phase in the temperature range of about 190° C. to 205° C.

Comparative Example 10

Synthesis of Compound RM-10

About 11.1 g of compound RM-10 (n=6) was obtained substantially according to the same method and condition as in Comparative Example 9, except that compound 14-b according to Comparative Example 8 was used instead of compound 14-a.

NMR spectrum of compound RM-10 is as follows.

$^1$H NMR (CDCl$_3$, standard material TMS) δ(ppm): 8.50 (2H, s), 8.19 (2H, d), 7.73 (2H, d), 7.62 (2H, d), 7.24 (4H, s), 7.00 (4H, m), 6.45 (2H, dd), 6.07 (2H, dd), 5.91 (2H, dd), 4.14 (4H, m), 4.04 (4H, m), 1.75 (4H, m), 1.51 (4H, m), 1.29 (8H, m)

And, the organization of compound RM-10 was observed with a polarizing microscope and the phase transition temperature was measured. As a result, it was recognized that compound RM-10 forms nematic phase in the temperature range of about 201° C. to 212° C.

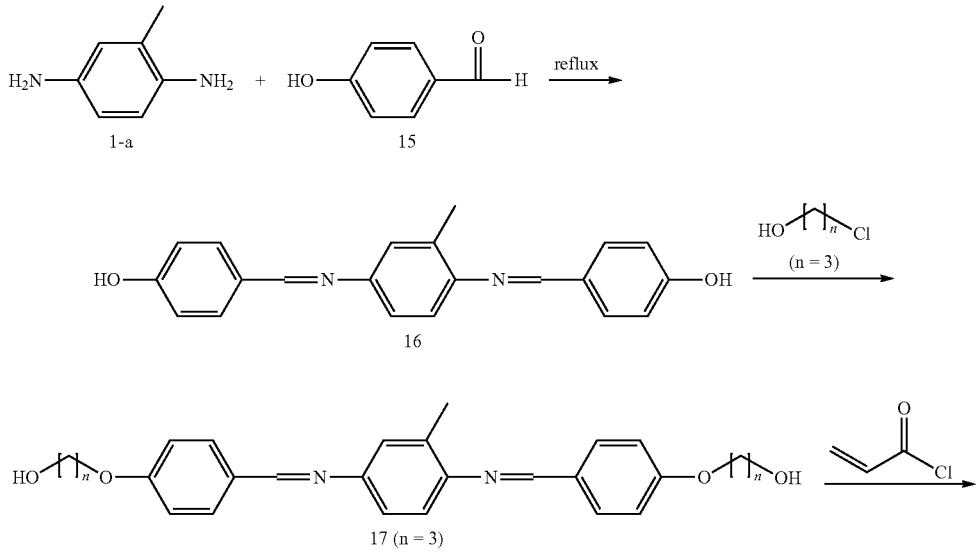

[Scheme 5: Comparative Examples 11 ~ 13]

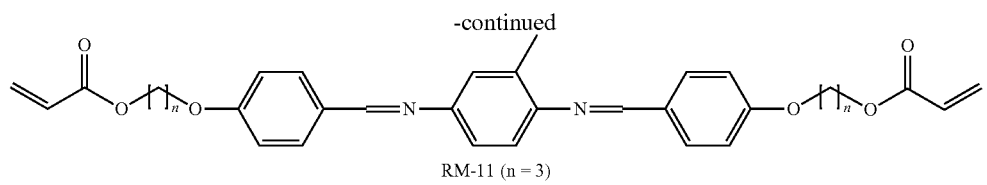

RM-11 (n = 3)

Comparative Example 11

Synthesis of Compound 16

About 22 g of compound 16 was obtained substantially according to the same method and condition as in Example 1, except that 4-hydroxybenzaldehyde (compound 15) was used instead of compound 2.

Comparative Example 12

Synthesis of Compound 17

About 15.3 g of compound 17 was obtained substantially according to the same method and condition as in Example 3, except that compound 17 according to Comparative Example 12 was used instead of compound 4-a.

NMR spectrum of compound RM-11 is as follows.

$^1$H NMR (CDCl$_3$, standard material TMS) δ(ppm): 8.39 (2H, s), 7.85 (4H, m), 7.30 (2H, m), 7.06 (4H, m), 6.46 (1H, d), 6.27 (2H, dd), 6.05 (2H, dd), 5.59 (2H, dd), 4.20 (8H, m), 2.36 (3H, s), 2.10 (4H, m)

And, the organization of compound RM-11 was observed with a polarizing microscope and the phase transition temperature was measured. As a result, it was recognized that compound RM-11 forms nematic phase in the temperature range of about 103° C. to 132° C.

[Scheme 6: Comparative Examples 14 ~ 15]

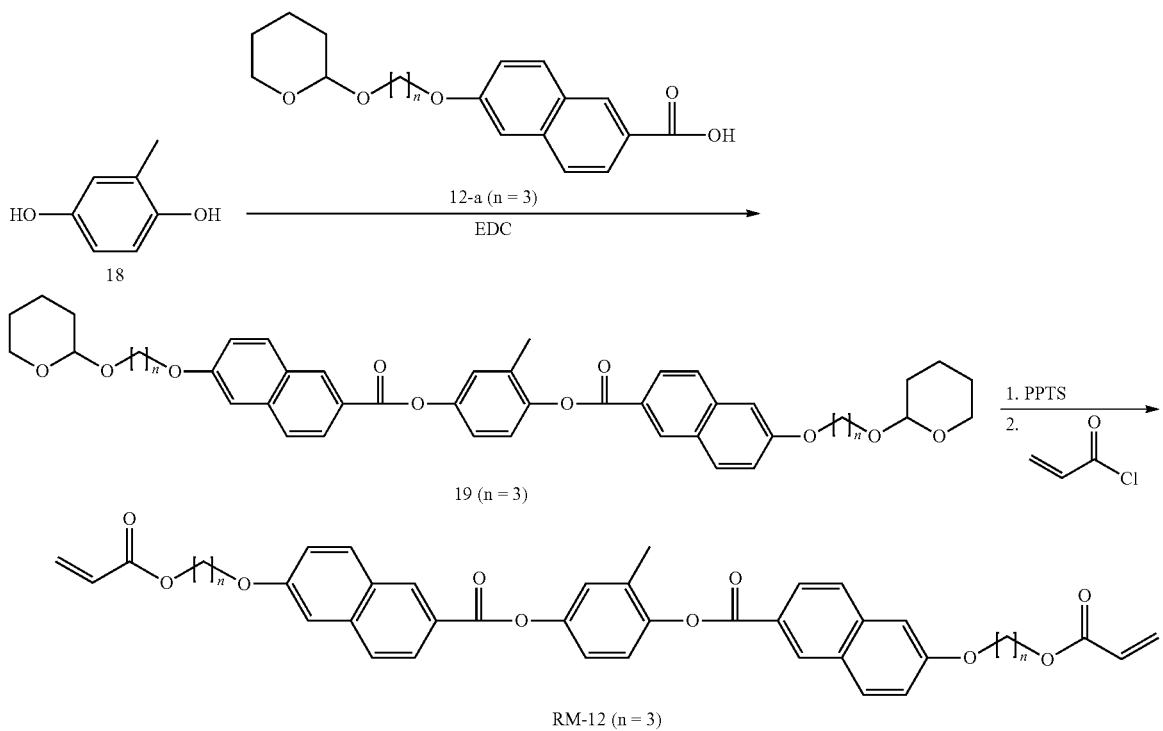

except that compound 16 according to Comparative Example 11 was used instead of compound 3-a.

Comparative Example 13

Synthesis of Compound RM-11

About 12 g of compound RM-11 was obtained substantially according to the same method and condition as in

Comparative Example 14

Synthesis of Compound 19

About 15 g of compound 19 was obtained substantially according to the same method and condition as in Comparative Example 7, except that 2-methylbenzene-1,4-diol (compound 18) was used instead of compound 13.

Comparative Example 15

Synthesis of Compound RM-12

About 9 g of compound RM-12 was obtained substantially according to the same method and condition as in Comparative Example 9, except that compound 19 according to Comparative Example 14 was used instead of compound 14-a.

NMR spectrum of compound RM-12 is as follows.

$^1$H NMR (CDCl$_3$, standard material TMS) δ(ppm): 8.64 (2H, s), 8.32 (2H, d), 7.92 (4H, d), 7.88 (4H, d), 7.42 (3H, m), 6.43 (2H, dd), 6.04 (2H, dd), 5.92 (2H, dd), 4.16 (4H, m), 4.03 (4H, m), 2.15 (3H, s), 1.75 (4H, m), 1.49 (4H, m), 1.29 (8H, m)

And, the organization of compound RM-12 was observed with a polarizing microscope and the phase transition temperature was measured. As a result, it was recognized that compound RM-12 forms nematic phase in the temperature range of about 198° C. to 210° C.

Preparation Examples 1~8

Preparation of Retardation Film

A polymerizable liquid crystal composition including 25 parts by weight of compound RM-01, 5 parts by weight of photoinitiator (Irgacure 907, made by Ciba-Geigy Co., Swiss), and the rest amount of CPO(cyclopentanone) per 100 parts by weight of total composition was prepared.

The liquid crystal composition coated with a roll coating method on a COP (cycloolefin polymer) film on which norbornene-based photoaligning material was coated, and dried at about 90° C. for 2 mins so as that the liquid crystal compound was aligned. And then, the retardation film was prepared by exposing the film to a non-polarized UV from a high pressure mercury lamp of 200 mW/cm$^2$ so as to fixing the oriented state of the liquid crystal.

As in above method, the compositions including any one of compounds RM-02 to RM-08 instead of compound RM-01 were prepared, and the retardation films were prepared respectively by using the same.

Comparative Preparation Examples 1~4

Preparation of Retardation Film

The retardation films were prepared substantially according to the same method as in Preparation Examples 1~8, except that compounds RM-09, RM-10, RM-11, and RM-12 of Comparative Examples were used respectively instead of compound RM-01.

Reference Example

The retardation film was prepared substantially according to the same method as in Preparation Examples 1~8, except that the polymerizable liquid crystal compound (RM 257, made by XI'AN RUILIAN MODERN Co., Ltd) represented by the following Chemical Formula 10 was used instead of compound RM-01:

Experimental Example 1

Quantitative retardation values of the retardation films according to Preparation Examples 1~8, Comparative Preparation Examples 1~4, and Reference Example were measured by using Axoscan (made by Axomatrix Co.). At this time, the thickness of the film was independently measured and Δn was calculated from the obtained values. The results are listed in Table 1.

Experimental Example 2

Figure 2:
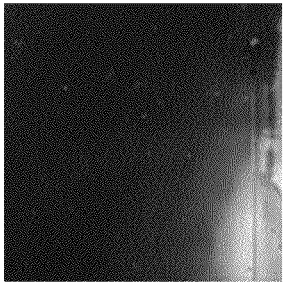
Figure 2:
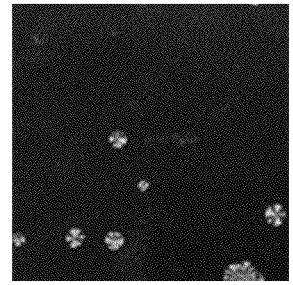
Figure 2:
Figure 2:
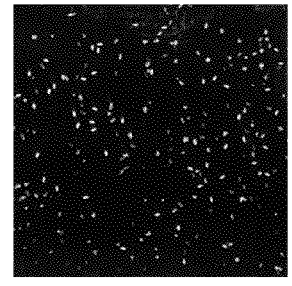
Figure 2:
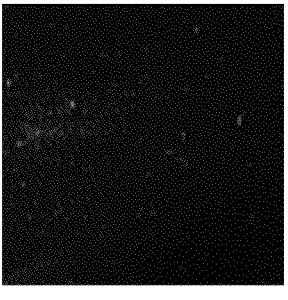

The light leakage was measured by taking photos with ECLIPSE LV100POL (made by NIKON Co.) after positioning each retardation films according to Preparation Examples 1~8, Comparative Preparation Examples 1~4, and Reference Example between two polarizers which are aligned perpendicularly. The photos classified by compounds are shown in FIGS. 1 and 2.

TABLE 1

| Compound | Δn | Compound | Δn |
|---|---|---|---|
| RM-01 | 0.17 | RM-02 | 0.18 |
| RM-03 | 0.16 | RM-04 | 0.18 |
| RM-05 | 0.18 | RM-06 | 0.18 |
| RM-07 | 0.17 | RM-08 | 0.19 |
| RM-09 | — | RM-10 | — |
| RM-11 | 0.13 | RM-12 | — |
| RM257 | 0.12 | | |

As shown in Table 1, it was impossible to measure the accurate birefringence value of the retardation films including compound RM-09, RM-10, or RM-12 because the compounds were not uniformly aligned in the preparation process. Furthermore, compound RM-11 including imine connecting group but not including naphthalene ring in the main chain showed satisfactory orientation but it showed low birefringence similar to compound RM257.

By comparison, it was recognized that the retardation films including compounds RM-01 to RM-08 according to Preparation Examples 1~8 have higher birefringence than prior films.

Furthermore, as shown in FIGS. 1 and 2, it was recognized that the retardation films including compounds RM-01 to RM-08 according to Preparation Examples 1~8 hardly show light leakage phenomenon in comparison to the films of Comparative Preparation Examples 1~4 and Reference Example.

What is claimed is:

1. A polymerizable liquid crystal compound represented by the following Chemical Formula 1 is provided:

[Chemical Formula 10]

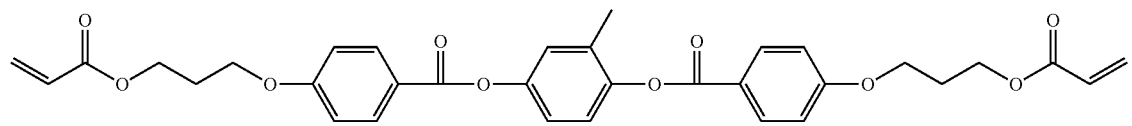

[Chemical Formula 1]

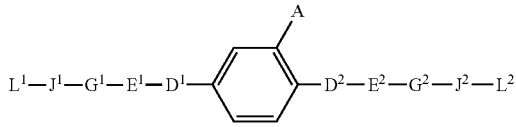

in Chemical Formula 1,

A is a $C_1$-$C_{10}$ alkyl group;

$D^1$, $D^2$, $G^1$, and $G^2$ are independently a single bond or a divalent connecting group, and at least one of $D^1$, $D^2$, $G^1$, and $G^2$ is an imine group;

$E^1$ and $E^2$ are independently benzene ring or naphthalene ring, and at least one of $E^1$ and $E^2$ is naphthalene ring;

$J^1$ and $J^2$ are independently a $C_1$-$C_{10}$ alkylene group; and $L^1$ and $L^2$ are independently hydrogen or a polymerizable group, wherein at least one of the $L^1$ and $L^2$ is the polymerizable group.

2. The polymerizable liquid crystal compound according to claim 1, showing at least one peak at the chemical shift (δ) of 8.0 ppm to 8.5 ppm in $^1$H NMR spectrum.

3. The polymerizable liquid crystal compound according to claim 1,
wherein $D^1$, $D^2$, $G^1$, and $G^2$ are independently a single bond, —CH=N—, —O—, —S—, —CO—, —COO—, —OCO—, —O—COO—, —CO—NR—, —NR—CO—, —NR—CO—NR—, —OCH$_2$—, —CH$_2$O—, —SCH—, —CH$_2$S—, —CF$_2$O—, —OCF$_2$—, —CF$_2$S—, —SCF$_2$—, —CH$_2$CH$_2$—, —(CH$_2$)$_3$—, —(CH$_2$)$_4$—, —CF$_2$CH$_2$—, —CH$_2$CF$_2$—, —CF$_2$CF$_2$—, —C=C—, or —C≡C—, and said R is independently hydrogen or a $C_1$-$C_{10}$ alkyl group; and
at least one of $D^1$, $D^2$, $G^1$, and $G^2$ is imine group (—CH=N—).

4. The polymerizable liquid crystal compound according to claim 1, wherein each of $E^1$ and $E^2$ is naphthalene ring.

5. The polymerizable liquid crystal compound according to claim 1, wherein each of $L^1$ and $L^2$ is independently hydrogen, an acrylate, a methacrylate, or an epoxy, and at least one of the $L^1$ and $L^2$ is the acrylate, the methacrylate, or the epoxy.

6. A polymerizable liquid crystal composition, including the compound according to claim 1.

7. The polymerizable liquid crystal composition according to claim 6, further including a polymerization initiator and a solvent.

8. An optically anisotropic body, including the polymerizable liquid crystal compound of Chemical Formula 1 according to claim 1.

9. The optically anisotropic body according to claim 8, including a hardened material or polymer in which at least part of the end polymerizable groups of the polymerizable liquid crystal compound of Chemical Formula 1 is addition-polymerized or cross-linked.

10. An optical element for liquid crystal display, including the optically anisotropic body according to claim 8.

* * * * *